United States Patent
Han et al.

(10) Patent No.: US 11,203,743 B2
(45) Date of Patent: Dec. 21, 2021

(54) METHOD FOR PRODUCING LONG-CHAIN GLYCOSYLATED GENISTEIN

(71) Applicant: Jiangnan University, Wuxi (CN)

(72) Inventors: Ruizhi Han, Wuxi (CN); Ye Ni, Wuxi (CN); Baocheng Chai, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/123,226

(22) Filed: Dec. 16, 2020

(65) Prior Publication Data

US 2021/0108182 A1 Apr. 15, 2021

Related U.S. Application Data

(63) Continuation of application No. PCT/CN2020/091254, filed on May 20, 2020.

(30) Foreign Application Priority Data

Nov. 8, 2019 (CN) .......................... 201911084700.2
Nov. 8, 2019 (CN) .......................... 201911084769.5

(51) Int. Cl.
*C12N 9/10* (2006.01)
*C12P 19/60* (2006.01)
*C12P 19/18* (2006.01)

(52) U.S. Cl.
CPC ............ *C12N 9/1074* (2013.01); *C12P 19/18* (2013.01); *C12P 19/60* (2013.01); *C12Y 204/01019* (2013.01)

(58) Field of Classification Search
CPC .................................. C12P 9/18; C12N 9/1074
See application file for complete search history.

(56) References Cited

U.S. PATENT DOCUMENTS 6,184,001 B1 2/2001 Starnes
2006/0075522 A1 4/2006 Cleveland et al.

FOREIGN PATENT DOCUMENTS

| CN | 106754604 A | 5/2017 |
| CN | 106755215 A | 5/2017 |
| CN | 108486080 A | 9/2018 |
| CN | 108531466 A | 9/2018 |
| CN | 110734946 A | 1/2020 |
| CN | 110804597 A | 2/2020 |

OTHER PUBLICATIONS

Han R,Engineering of Cyclodextrin Glycosyltransferase Reveals pH-Regulated Mechanism of Enhanced Long-Chain Glycosylated Sophoricoside Specificity, Applied and environmental microbiology, Mar. 18, 2020, vol. 7 Issue 26 p. 1-14.

Primary Examiner — Robert J Yamasaki
Assistant Examiner — Charles Zoltan Constantine
(74) Attorney, Agent, or Firm — IPRO, PLLC; Na Xu

(57) ABSTRACT

The disclosure discloses a method for producing long-chain glycosylated genistein and belongs to the technical fields of enzyme engineering and fermentation engineering. The disclosure provides a method for producing long-chain glycosylated genistein. By using this method to produce long-chain glycosylated genistein, the content of long-chain glycosylated genistein in a reaction solution and the ratio of the content of long-chain glycosylated genistein in the reaction solution to the content of total glycosylated genistein in the reaction solution can be increased. The content of long-chain glycosylated genistein in the reaction solution can be increased to 10.3 g/L, and the ratio of the content of long-chain glycosylated genistein in the reaction solution to the content of total glycosylated genistein in the reaction solution can be increased to 70%.

16 Claims, 1 Drawing Sheet

Specification includes a Sequence Listing.

SEQUENCE LISTING

```
<160> NUMBER OF SEQ ID NOS: 25

<210> SEQ ID NO 1
<211> LENGTH: 687
<212> TYPE: PRT
<213> ORGANISM: Artificial sequence
<220> FEATURE:
<223> OTHER INFORMATION: Translated from synthetic DNA

<400> SEQUENCE: 1

Ser Pro Asp Thr Ser Val Asp Asn Lys Val Asn Phe Ser Thr Asp Val
1               5                   10                  15

Ile Tyr Gln Ile Val Thr Asp Arg Phe Ala Asp Gly Asp Arg Thr Asn
            20                  25                  30

Asn Pro Ala Gly Asp Ala Phe Ser Gly Asp Arg Ser Asn Leu Lys Leu
        35                  40                  45

Tyr Phe Gly Gly Asp Trp Gln Gly Ile Ile Asp Lys Ile Asn Asp Gly
    50                  55                  60
```

```
Tyr Leu Thr Gly Met Gly Val Thr Ala Leu Trp Ile Ser Gln Pro Val
 65                  70                  75                  80

Glu Asn Ile Thr Ser Val Ile Lys Tyr Ser Gly Val Asn Asn Thr Ser
                 85                  90                  95

Tyr His Gly Tyr Trp Ala Arg Asp Phe Lys Gln Thr Asn Asp Ala Phe
            100                 105                 110

Gly Asp Phe Ala Asp Phe Gln Asn Leu Ile Asp Thr Ala His Ala His
        115                 120                 125

Asn Ile Lys Val Val Ile Asp Phe Ala Pro Asn His Thr Ser Pro Ala
    130                 135                 140

Asp Arg Asp Asn Pro Gly Phe Ala Glu Asn Gly Ala Leu Tyr Asp Asn
145                 150                 155                 160

Gly Ser Leu Leu Gly Ala Tyr Ser Asn Asp Thr Ala Gly Leu Phe His
            165                 170                 175

His Asn Gly Gly Thr Asp Phe Ser Thr Ile Glu Asp Gly Ile Tyr Lys
        180                 185                 190

Asn Leu Tyr Asp Leu Ala Asp Ile Asn His Asn Asn Ala Met Asp
    195                 200                 205

Ala Tyr Phe Lys Ser Ala Ile Asp Leu Trp Leu Gly Met Gly Val Asp
210                 215                 220

Gly Ile Arg Phe Asp Ala Val Lys His Met Pro Phe Gly Trp Gln Lys
225                 230                 235                 240

Ser Phe Val Ser Ser Ile Tyr Gly Gly Asp His Pro Val Phe Thr Phe
            245                 250                 255

Gly Glu Trp Tyr Leu Gly Ala Asp Gln Thr Asp Gly Asp Asn Ile Lys
        260                 265                 270

Phe Ala Asn Glu Ser Gly Met Asn Leu Leu Asp Phe Glu Tyr Ala Gln
    275                 280                 285

Glu Val Arg Glu Val Phe Arg Asp Lys Thr Glu Thr Met Lys Asp Leu
290                 295                 300

Tyr Glu Val Leu Ala Ser Thr Glu Ser Gln Tyr Asp Tyr Ile Asn Asn
305                 310                 315                 320

Met Val Thr Phe Ile Asp Asn His Asp Met Asp Arg Phe Gln Val Ala
            325                 330                 335

Gly Ser Gly Thr Arg Ala Thr Glu Gln Ala Leu Ala Leu Thr Leu Thr
        340                 345                 350

Ser Arg Gly Val Pro Ala Ile Tyr Tyr Gly Thr Glu Gln Tyr Met Thr
    355                 360                 365

Gly Asp Gly Asp Pro Asn Asn Arg Ala Met Met Thr Ser Phe Asn Thr
370                 375                 380

Gly Thr Thr Ala Tyr Lys Val Ile Gln Ala Leu Ala Pro Leu Arg Lys
385                 390                 395                 400

Ser Asn Pro Ala Ile Ala Tyr Gly Thr Thr Glu Arg Trp Val Asn
            405                 410                 415

Asn Asp Val Leu Ile Ile Glu Arg Lys Phe Gly Ser Ser Ala Ala Leu
        420                 425                 430

Val Ala Ile Asn Arg Asn Ser Ser Ala Ala Tyr Pro Ile Ser Gly Leu
    435                 440                 445

Leu Ser Ser Leu Pro Ala Gly Thr Tyr Ser Asp Val Leu Asn Gly Leu
450                 455                 460

Leu Asn Gly Asn Ser Ile Thr Val Gly Ser Gly Gly Ala Val Thr Asn
465                 470                 475                 480
```

Phe Thr Leu Ala Ala Gly Gly Thr Ala Val Trp Gln Tyr Thr Ala Pro
                485                 490                 495

Glu Thr Ser Pro Ala Ile Gly Asn Val Gly Pro Thr Met Gly Gln Pro
            500                 505                 510

Gly Asn Ile Val Thr Ile Asp Gly Arg Gly Phe Gly Gly Thr Ala Gly
            515                 520                 525

Thr Val Tyr Phe Gly Thr Thr Ala Val Thr Gly Ser Gly Ile Val Ser
        530                 535                 540

Trp Glu Asp Thr Gln Ile Lys Ala Val Ile Pro Lys Val Ala Ala Gly
545                 550                 555                 560

Lys Thr Gly Val Ser Val Lys Thr Ser Ser Gly Thr Ala Ser Asn Thr
                565                 570                 575

Phe Lys Ser Phe Asn Val Leu Thr Gly Asp Gln Val Thr Val Arg Phe
            580                 585                 590

Leu Val Asn Gln Ala Asn Thr Asn Tyr Gly Thr Asn Val Tyr Leu Val
        595                 600                 605

Gly Asn Ala Ala Glu Leu Gly Ser Trp Asp Pro Asn Lys Ala Ile Gly
        610                 615                 620

Pro Met Tyr Asn Gln Val Ile Ala Lys Tyr Pro Ser Trp Tyr Tyr Asp
625                 630                 635                 640

Val Ser Val Pro Ala Gly Thr Lys Leu Asp Phe Lys Phe Ile Lys Lys
                645                 650                 655

Gly Gly Gly Thr Val Thr Trp Glu Gly Gly Asn His Thr Tyr Thr
            660                 665                 670

Thr Pro Ala Ser Gly Val Gly Thr Val Thr Val Asp Trp Gln Asn
        675                 680                 685

<210> SEQ ID NO 2
<211> LENGTH: 2061
<212> TYPE: DNA
<213> ORGANISM: Artificial sequence
<220> FEATURE:
<223> OTHER INFORMATION: Synthestic DNA

<400> SEQUENCE: 2
tcaccggaca cctcagtgga caataaagtt aacttcagca ccgatgttat ctaccagatc      60
gtcacggacc gttttgcgga tggtgaccgc accaacaatc cggcaggcga tgctttcagc     120
ggtgaccgtt ctaatctgaa actgtatttt ggcggtgatt ggcagggcat tatcgataaa     180
attaacgacg gttacctgac cggcatgggt gtgacggcgc tgtggatcag ccaaccggtg     240
gaaaacatca cctcagttat caaatactcg ggcgtcaaca atacgtctta tcatggttac     300
tgggcccgtg attttaaaca gaccaacgac gcgtttggcg atttcgccga ctttcaaaat     360
ctgattgata ccgcacatgc tcacaacatt aaagtggtta tcgatttcgc cccgaaccac     420
acctctccgg cagatcgcga caatccgggc tttgcagaaa atggtgctct gtatgataac     480
ggctcactgc tgggtgcata ctcgaatgac accgctggcc tgttccatca caacggcggt     540
acggatttta gtaccattga agacggtatc tataaaaatc tgtacgatct ggctgacatc     600
aaccataaca ataacgcgat ggatgcctat ttcaaatcag caattgacct gtggctgggc     660
atgggtgttg atggcatccg ctttgacgcg gtcaaacaca tgccgttcgg ttggcagaaa     720
tcgtttgtga gcagcattta tggcggtgat cacccggttt ttaccttcgg cgaatggtat     780
ctgggtgcta tcagacgga tggcgacaat atcaaatttg cgaacgaatc tggtatgaat     840
ctgctggatt ttgaatatgc acaagaagtc cgtgaagtgt ttcgcgataa aacggaaacc     900

```
atgaaagacc tgtacgaagt gctggcctca accgaatcgc agtatgatta cattaataac    960
atggtgacct tcatcgacaa tcacgatatg gaccgttttc aggttgcggg ctcaggtacg   1020
cgcgccaccg aacaagcgct ggcactgacg ctgacctcgc gtggcgttcc ggcgatttat   1080
tacggcaccg aacagtatat gacgggcgat ggtgacccga taaccgcgc catgatgacg   1140 agtttcaata ccggcaccac ggcatataaa gtgattcaag cactggctcc gctgcgtaaa   1200
tccaacccgg caatcgccta cggcaccacc accgaacgtt gggtgaataa cgatgttctg   1260
attatcgaac gcaaatttgg tagttccgcg gccctggtcg ccattaatcg caactcatcg   1320
gcagcttatc cgatcagtgg tctgctgagc agcctgccag cgggcaccta ctccgatgtg   1380
ctgaatggcc tgctgaatgg taacagcatt accgtgggct ctggcggtgc ggttacgaac   1440
tttaccctgg cagcgggcgg caccgcagtt tggcagtata cggctccgga accagcccg   1500 gcgatcggta atgtcggtcc gacgatgggc caaccgggta acattgtgac gatcgatggt   1560
cgtggtttcg gcggtacggc tggcaccgtg tactttggta cgaccgcggt caccggcagt   1620
ggtattgtgt cctgggaaga tacgcagatt aaagcggtca tcccgaaagt ggcagctggc   1680
aaaaccggtg tcagcgtgaa acgagttcc ggcaccgcca gtaatacgtt caaatccttt   1740
aacgttctga ccggtgatca ggttacggtc cgctttctgg tcaaccaagc gaataccaac   1800
tatggcacga atgtttacct ggtcggcaac gcggccgaac tgggttcctg gacccgaat    1860 aaagccattg gtccgatgta taccaggtt atcgcaaaat acccgagctg gtattacgat   1920
gtgagcgttc cggcgggcac caaactggac ttcaaattca ttaaaaaagg cggtggcacg   1980
gtgacctggg aaggtggcgg taaccatacc tacacgaccc cggcgagcgg cgttggcacg   2040
gtgacggtgg attggcaaaa t                                              2061
```

<210> SEQ ID NO 3
<211> LENGTH: 687
<212> TYPE: PRT
<213> ORGANISM: Artificial sequence
<220> FEATURE:
<223> OTHER INFORMATION: Translated from synthetic DNA

<400> SEQUENCE: 3

```
Ser Pro Asp Thr Ser Val Asp Asn Lys Val Asn Phe Ser Thr Asp Val
1               5                   10                  15

Ile Tyr Gln Ile Val Thr Asp Arg Phe Ala Asp Gly Asp Arg Thr Asn
            20                  25                  30

Asn Pro Ala Gly Asp Ala Phe Ser Gly Asp Arg Ser Asn Leu Lys Leu
        35                  40                  45

Tyr Phe Gly Gly Asp Trp Gln Gly Ile Ile Asp Lys Ile Asn Asp Gly
    50                  55                  60

Tyr Leu Thr Gly Met Gly Val Thr Ala Leu Trp Ile Ser Gln Pro Val
65                  70                  75                  80

Glu Asn Ile Thr Ser Val Ile Lys Tyr Ser Gly Val Asn Asn Thr Ser
                85                  90                  95

Tyr His Gly Tyr Trp Ala Arg Asp Phe Lys Gln Thr Asn Asp Ala Phe
            100                 105                 110

Gly Asp Phe Ala Asp Phe Gln Asn Leu Ile Asp Thr Ala His Ala His
        115                 120                 125

Asn Ile Lys Val Val Ile Asp Phe Ala Pro Asn His Thr Ser Pro Ala
    130                 135                 140

Asp Arg Asp Asn Pro Gly Phe Ala Glu Asn Gly Val Leu Tyr Asp Asn
145                 150                 155                 160
```

-continued

```
Gly Ser Leu Leu Gly Ala Tyr Ser Asn Asp Thr Ala Gly Pro Phe His
            165                 170                 175
His Asn Gly Gly Thr Asp Phe Ser Thr Ile Glu Asp Gly Ile Tyr Lys
        180                 185                 190
Asn Leu Tyr Asp Leu Ala Asp Ile Asn His Asn Asn Asn Ala Met Asp
            195                 200                 205
Ala Tyr Phe Lys Ser Ala Ile Asp Leu Trp Leu Gly Met Gly Val Asp
        210                 215                 220
Gly Ile Arg Phe Asp Ala Val Lys His Met Pro Phe Gly Trp Gln Lys
225                 230                 235                 240
Ser Phe Val Ser Ser Ile Tyr Gly Gly Asp His Pro Val Phe Thr Phe
            245                 250                 255
Gly Glu Trp Tyr Leu Gly Ala Asp Gln Thr Asp Gly Asp Asn Ile Lys
        260                 265                 270
Phe Ala Asn Glu Ser Gly Met Asn Leu Leu Asp Phe Glu Tyr Ala Gln
            275                 280                 285
Glu Val Arg Glu Val Phe Arg Asp Lys Thr Glu Thr Met Lys Asp Leu
        290                 295                 300
Tyr Glu Val Leu Ala Ser Thr Glu Ser Gln Tyr Asp Tyr Ile Asn Asn
305                 310                 315                 320
Met Val Thr Phe Ile Asp Asn His Asp Met Asp Arg Phe Gln Val Ala
                325                 330                 335
Gly Ser Gly Thr Arg Ala Thr Glu Gln Ala Leu Ala Leu Thr Leu Thr
            340                 345                 350
Ser Arg Gly Val Pro Ala Ile Tyr Tyr Gly Thr Glu Gln Tyr Met Thr
        355                 360                 365
Gly Asp Gly Asp Pro Asn Asn Arg Ala Met Met Thr Ser Phe Asn Thr
    370                 375                 380
Gly Thr Thr Ala Tyr Lys Val Ile Gln Ala Leu Ala Pro Leu Arg Lys
385                 390                 395                 400
Ser Asn Pro Ala Ile Ala Tyr Gly Thr Thr Thr Glu Arg Trp Val Asn
                405                 410                 415
Asn Asp Val Leu Ile Ile Glu Arg Lys Phe Gly Ser Ser Ala Ala Leu
            420                 425                 430
Val Ala Ile Asn Arg Asn Ser Ser Ala Ala Tyr Pro Ile Ser Gly Leu
        435                 440                 445
Leu Ser Ser Leu Pro Ala Gly Thr Tyr Ser Asp Val Leu Asn Gly Leu
    450                 455                 460
Leu Asn Gly Asn Ser Ile Thr Val Gly Ser Gly Gly Ala Val Thr Asn
465                 470                 475                 480
Phe Thr Leu Ala Ala Gly Gly Thr Ala Val Trp Gln Tyr Thr Ala Pro
                485                 490                 495
Glu Thr Ser Pro Ala Ile Gly Asn Val Gly Pro Thr Met Gly Gln Pro
            500                 505                 510
Gly Asn Ile Val Thr Ile Asp Gly Arg Gly Phe Gly Gly Thr Ala Gly
        515                 520                 525
Thr Val Tyr Phe Gly Thr Thr Ala Val Thr Gly Ser Gly Ile Val Ser
    530                 535                 540
Trp Glu Asp Thr Gln Ile Lys Ala Val Ile Pro Lys Val Ala Ala Gly
545                 550                 555                 560
Lys Thr Gly Val Ser Val Lys Thr Ser Ser Gly Thr Ala Ser Asn Thr
                565                 570                 575
```

```
Phe Lys Ser Phe Asn Val Leu Thr Gly Asp Gln Val Thr Val Arg Phe
                580                 585                 590

Leu Val Asn Gln Ala Asn Thr Asn Tyr Gly Thr Asn Val Tyr Leu Val
            595                 600                 605

Gly Asn Ala Ala Glu Leu Gly Ser Trp Asp Pro Asn Lys Ala Ile Gly
        610                 615                 620

Pro Met Tyr Asn Gln Val Ile Ala Lys Tyr Pro Ser Trp Tyr Tyr Asp
625                 630                 635                 640

Val Ser Val Pro Ala Gly Thr Lys Leu Asp Phe Lys Phe Ile Lys Lys
                645                 650                 655

Gly Gly Gly Thr Val Thr Trp Glu Gly Gly Asn His Thr Tyr Thr
            660                 665                 670

Thr Pro Ala Ser Gly Val Gly Thr Val Thr Val Asp Trp Gln Asn
        675                 680                 685

<210> SEQ ID NO 4
<211> LENGTH: 687
<212> TYPE: PRT
<213> ORGANISM: Artificial sequence
<220> FEATURE:
<223> OTHER INFORMATION: Translated from synthetic DNA

<400> SEQUENCE: 4

Ser Pro Asp Thr Ser Val Asp Asn Lys Val Asn Phe Ser Thr Asp Val
1               5                   10                  15

Ile Tyr Gln Ile Val Thr Asp Arg Phe Ala Asp Gly Asp Arg Thr Asn
            20                  25                  30

Asn Pro Ala Gly Asp Ala Phe Ser Gly Asp Arg Ser Asn Leu Lys Leu
        35                  40                  45

Tyr Phe Gly Gly Asp Trp Gln Gly Ile Ile Asp Lys Ile Asn Asp Gly
50                  55                  60

Tyr Leu Thr Gly Met Gly Val Thr Ala Leu Trp Ile Ser Gln Pro Val
65                  70                  75                  80

Glu Asn Ile Thr Ser Val Ile Lys Tyr Ser Gly Val Asn Asn Thr Ser
                85                  90                  95

Tyr His Gly Tyr Trp Ala Arg Asp Phe Lys Gln Thr Asn Asp Ala Phe
            100                 105                 110

Gly Asp Phe Ala Asp Phe Gln Asn Leu Ile Asp Thr Ala His Ala His
        115                 120                 125

Asn Ile Lys Val Val Ile Asp Phe Ala Pro Asn His Thr Ser Pro Ala
130                 135                 140

Asp Arg Asp Asn Pro Gly Phe Ala Glu Asn Gly Val Leu Tyr Asp Asn
145                 150                 155                 160

Gly Ser Leu Leu Gly Tyr Tyr Ser Asn Asp Thr Ala Gly Pro Phe His
                165                 170                 175

His Asn Gly Gly Thr Asp Phe Ser Thr Ile Glu Asp Gly Ile Tyr Lys
            180                 185                 190

Asn Leu Tyr Asp Leu Ala Asp Ile Asn His Asn Asn Asn Ala Met Asp
        195                 200                 205

Ala Tyr Phe Lys Ser Ala Ile Asp Leu Trp Leu Gly Met Gly Val Asp
210                 215                 220

Gly Ile Arg Phe Asp Ala Val Lys His Met Pro Phe Gly Trp Gln Lys
225                 230                 235                 240

Ser Phe Val Ser Ser Ile Tyr Gly Gly Asp His Pro Val Phe Thr Phe
                245                 250                 255
```

-continued

```
Gly Glu Trp Tyr Leu Gly Ala Asp Gln Thr Asp Gly Asp Asn Ile Lys
            260                 265                 270

Phe Ala Asn Glu Ser Gly Met Asn Leu Leu Asp Phe Glu Tyr Ala Gln
            275                 280                 285

Glu Val Arg Glu Val Phe Arg Asp Lys Thr Glu Thr Met Lys Asp Leu
            290                 295                 300

Tyr Glu Val Leu Ala Ser Thr Glu Ser Gln Tyr Asp Tyr Ile Asn Asn
305                 310                 315                 320

Met Val Thr Phe Ile Asp Asn His Asp Met Asp Arg Phe Gln Val Ala
                325                 330                 335

Gly Ser Gly Thr Arg Ala Thr Glu Gln Ala Leu Ala Leu Thr Leu Thr
            340                 345                 350

Ser Arg Gly Val Pro Ala Ile Tyr Tyr Gly Thr Glu Gln Tyr Met Thr
            355                 360                 365

Gly Asp Gly Asp Pro Asn Asn Arg Ala Met Met Thr Ser Phe Asn Thr
            370                 375                 380

Gly Thr Thr Ala Tyr Lys Val Ile Gln Ala Leu Ala Pro Leu Arg Lys
385                 390                 395                 400

Ser Asn Pro Ala Ile Ala Tyr Gly Thr Thr Thr Glu Arg Trp Val Asn
                405                 410                 415

Asn Asp Val Leu Ile Ile Glu Arg Lys Phe Gly Ser Ser Ala Ala Leu
            420                 425                 430

Val Ala Ile Asn Arg Asn Ser Ser Ala Ala Tyr Pro Ile Ser Gly Leu
            435                 440                 445

Leu Ser Ser Leu Pro Ala Gly Thr Tyr Ser Asp Val Leu Asn Gly Leu
            450                 455                 460

Leu Asn Gly Asn Ser Ile Thr Val Gly Ser Gly Gly Ala Val Thr Asn
465                 470                 475                 480

Phe Thr Leu Ala Ala Gly Gly Thr Ala Val Trp Gln Tyr Thr Ala Pro
                485                 490                 495

Glu Thr Ser Pro Ala Ile Gly Asn Val Gly Pro Thr Met Gly Gln Pro
            500                 505                 510

Gly Asn Ile Val Thr Ile Asp Gly Arg Gly Phe Gly Gly Thr Ala Gly
            515                 520                 525

Thr Val Tyr Phe Gly Thr Thr Ala Val Thr Gly Ser Gly Ile Val Ser
            530                 535                 540

Trp Glu Asp Thr Gln Ile Lys Ala Val Ile Pro Lys Val Ala Ala Gly
545                 550                 555                 560

Lys Thr Gly Val Ser Val Lys Thr Ser Ser Gly Thr Ala Ser Asn Thr
                565                 570                 575

Phe Lys Ser Phe Asn Val Leu Thr Gly Asp Gln Val Thr Val Arg Phe
            580                 585                 590

Leu Val Asn Gln Ala Asn Thr Asn Tyr Gly Thr Asn Val Tyr Leu Val
            595                 600                 605

Gly Asn Ala Ala Glu Leu Gly Ser Trp Asp Pro Asn Lys Ala Ile Gly
            610                 615                 620

Pro Met Tyr Asn Gln Val Ile Ala Lys Tyr Pro Ser Trp Tyr Tyr Asp
625                 630                 635                 640

Val Ser Val Pro Ala Gly Thr Lys Leu Asp Phe Lys Phe Ile Lys Lys
                645                 650                 655
```

Gly Gly Gly Thr Val Thr Trp Glu Gly Gly Asn His Thr Tyr Thr
            660                 665                 670

Thr Pro Ala Ser Gly Val Gly Thr Val Thr Val Asp Trp Gln Asn
        675                 680                 685

<210> SEQ ID NO 5
<211> LENGTH: 687
<212> TYPE: PRT
<213> ORGANISM: Artificial sequence
<220> FEATURE:
<223> OTHER INFORMATION: Translated from synthetic DNA

<400> SEQUENCE: 5

Ser Pro Asp Thr Ser Val Asp Asn Lys Val Asn Phe Ser Thr Asp Val
1               5                   10                  15

Ile Tyr Gln Ile Val Thr Asp Arg Phe Ala Asp Gly Asp Arg Thr Asn
            20                  25                  30

Asn Pro Ala Gly Asp Ala Phe Ser Gly Asp Arg Ser Asn Leu Lys Leu
        35                  40                  45

Tyr Phe Gly Gly Asp Trp Gln Gly Ile Ile Asp Lys Ile Asn Asp Gly
50                  55                  60

Tyr Leu Thr Gly Met Gly Val Thr Ala Leu Trp Ile Ser Gln Pro Val
65                  70                  75                  80

Glu Asn Ile Thr Ser Val Ile Lys Tyr Ser Gly Val Asn Asn Thr Ser
                85                  90                  95

Tyr His Gly Tyr Trp Ala Arg Asp Phe Lys Gln Thr Asn Asp Ala Phe
            100                 105                 110

Gly Asp Phe Ala Asp Phe Gln Asn Leu Ile Asp Thr Ala His Ala His
        115                 120                 125

Asn Ile Lys Val Val Ile Asp Phe Ala Pro Asn His Thr Ser Pro Ala
130                 135                 140

Asp Arg Asp Asn Pro Gly Phe Ala Glu Asn Gly Val Leu Tyr Asp Asn
145                 150                 155                 160

Gly Ser Leu Leu Gly Val Tyr Ser Asn Asp Thr Ala Gly Pro Phe His
                165                 170                 175

His Asn Gly Gly Thr Asp Phe Ser Thr Ile Glu Asp Gly Ile Tyr Lys
            180                 185                 190

Asn Leu Tyr Asp Leu Ala Asp Ile Asn His Asn Asn Ala Met Asp
        195                 200                 205

Ala Tyr Phe Lys Ser Ala Ile Asp Leu Trp Leu Gly Met Gly Val Asp
210                 215                 220

Gly Ile Arg Phe Asp Ala Val Lys His Met Pro Phe Gly Trp Gln Lys
225                 230                 235                 240

Ser Phe Val Ser Ser Ile Tyr Gly Gly Asp His Pro Val Phe Thr Phe
                245                 250                 255

Gly Glu Trp Tyr Leu Gly Ala Asp Gln Thr Asp Gly Asp Asn Ile Lys
            260                 265                 270

Phe Ala Asn Glu Ser Gly Met Asn Leu Leu Asp Phe Glu Tyr Ala Gln
        275                 280                 285

Glu Val Arg Glu Val Phe Arg Asp Lys Thr Gly Thr Met Lys Asp Leu
290                 295                 300

Tyr Glu Val Leu Ala Ser Thr Glu Ser Gln Tyr Asp Tyr Ile Asn Asn
305                 310                 315                 320

```
Met Val Thr Phe Ile Asp Asn His Asp Met Asp Arg Phe Gln Val Ala
                325                 330                 335
Gly Ser Gly Thr Arg Ala Thr Glu Gln Ala Leu Ala Leu Thr Leu Thr
            340                 345                 350
Ser Arg Gly Val Pro Ala Ile Tyr Tyr Gly Thr Glu Gln Tyr Met Thr
        355                 360                 365
Gly Asp Gly Asp Pro Asn Asn Arg Ala Met Met Thr Ser Phe Asn Thr
    370                 375                 380
Gly Thr Thr Ala Tyr Lys Val Ile Gln Ala Leu Ala Pro Leu Arg Lys
385                 390                 395                 400
Ser Asn Pro Ala Ile Ala Tyr Gly Thr Thr Thr Glu Arg Trp Val Asn
                405                 410                 415
Asn Asp Val Leu Ile Ile Glu Arg Lys Phe Gly Ser Ser Ala Ala Leu
            420                 425                 430
Val Ala Ile Asn Arg Asn Ser Ser Ala Ala Tyr Pro Ile Ser Gly Leu
        435                 440                 445
Leu Ser Ser Leu Pro Ala Gly Thr Tyr Ser Asp Val Leu Asn Gly Leu
    450                 455                 460
Leu Asn Gly Asn Ser Ile Thr Val Gly Ser Gly Gly Ala Val Thr Asn
465                 470                 475                 480
Phe Thr Leu Ala Ala Gly Gly Thr Ala Val Trp Gln Tyr Thr Ala Pro
                485                 490                 495
Glu Thr Ser Pro Ala Ile Gly Asn Val Gly Pro Thr Met Gly Gln Pro
            500                 505                 510
Gly Asn Ile Val Thr Ile Asp Gly Arg Gly Phe Gly Gly Thr Ala Gly
        515                 520                 525
Thr Val Tyr Phe Gly Thr Thr Ala Val Thr Gly Ser Gly Ile Val Ser
    530                 535                 540
Trp Glu Asp Thr Gln Ile Lys Ala Val Ile Pro Lys Val Ala Ala Gly
545                 550                 555                 560
Lys Thr Gly Val Ser Val Lys Thr Ser Ser Gly Thr Ala Ser Asn Thr
                565                 570                 575
Phe Lys Ser Phe Asn Val Leu Thr Gly Asp Gln Val Thr Val Arg Phe
            580                 585                 590
Leu Val Asn Gln Ala Asn Thr Asn Tyr Gly Thr Asn Val Tyr Leu Val
        595                 600                 605
Gly Asn Ala Ala Glu Leu Gly Ser Trp Asp Pro Asn Lys Ala Ile Gly
    610                 615                 620
Pro Met Tyr Asn Gln Val Ile Ala Lys Tyr Pro Ser Trp Tyr Tyr Asp
625                 630                 635                 640
Val Ser Val Pro Ala Gly Thr Lys Leu Asp Phe Lys Phe Ile Lys Lys
                645                 650                 655
Gly Gly Gly Thr Val Thr Trp Glu Gly Gly Asn His Thr Tyr Thr
            660                 665                 670
Thr Pro Ala Ser Gly Val Gly Thr Val Thr Val Asp Trp Gln Asn
        675                 680                 685

<210> SEQ ID NO 6
<211> LENGTH: 687
<212> TYPE: PRT
<213> ORGANISM: Artificial sequence
<220> FEATURE:
<223> OTHER INFORMATION: Translated from synthetic DNA
```

```
<400> SEQUENCE: 6

Ser Pro Asp Thr Ser Val Asp Asn Lys Val Asn Phe Ser Thr Asp Val
1               5                   10                  15

Ile Tyr Gln Ile Val Thr Asp Arg Phe Ala Asp Gly Asp Arg Thr Asn
            20                  25                  30

Asn Pro Ala Gly Asp Ala Phe Ser Gly Asp Arg Ser Asn Leu Lys Leu
        35                  40                  45

Tyr Phe Gly Gly Asp Trp Gln Gly Ile Ile Asp Lys Ile Asn Asp Gly
    50                  55                  60

Tyr Leu Thr Gly Met Gly Val Thr Ala Leu Trp Ile Ser Gln Pro Val
65                  70                  75                  80

Glu Asn Ile Thr Ser Val Ile Lys Tyr Ser Gly Val Asn Asn Thr Ser
                85                  90                  95

Tyr His Gly Tyr Trp Ala Arg Asp Phe Lys Gln Thr Asn Asp Ala Phe
            100                 105                 110

Gly Asp Phe Ala Asp Phe Gln Asn Leu Ile Asp Thr Ala His Ala His
        115                 120                 125

Asn Ile Lys Val Val Ile Asp Phe Ala Pro Asn His Thr Ser Pro Ala
130                 135                 140

Asp Arg Asp Asn Pro Gly Phe Ala Glu Asn Gly Val Leu Tyr Asp Asn
145                 150                 155                 160

Gly Ser Leu Leu Gly Gly Tyr Ser Asn Asp Thr Ala Gly Pro Phe His
                165                 170                 175

His Asn Gly Gly Thr Asp Phe Ser Thr Ile Glu Asp Gly Ile Tyr Lys
            180                 185                 190

Asn Leu Tyr Asp Leu Ala Asp Ile Asn His Asn Asn Asn Ala Met Asp
        195                 200                 205

Ala Tyr Phe Lys Ser Ala Ile Asp Leu Trp Leu Gly Met Gly Val Asp
    210                 215                 220

Gly Ile Arg Phe Asp Ala Val Lys His Met Pro Phe Gly Trp Gln Lys
225                 230                 235                 240

Ser Phe Val Ser Ser Ile Tyr Gly Gly Asp His Pro Val Phe Thr Phe
                245                 250                 255

Gly Glu Trp Tyr Leu Gly Ala Asp Gln Thr Asp Gly Asp Asn Ile Lys
            260                 265                 270

Phe Ala Asn Glu Ser Gly Met Asn Leu Leu Asp Phe Glu Tyr Ala Gln
        275                 280                 285

Glu Val Arg Glu Val Phe Arg Asp Lys Thr Glu Thr Met Lys Asp Leu
    290                 295                 300

Tyr Glu Val Leu Ala Ser Thr Glu Ser Gln Tyr Asp Tyr Ile Asn Asn
305                 310                 315                 320

Met Val Thr Phe Ile Asp Asn His Asp Met Asp Arg Phe Gln Val Ala
                325                 330                 335

Gly Ser Gly Thr Arg Ala Thr Glu Gln Ala Leu Ala Leu Thr Leu Thr
            340                 345                 350

Ser Arg Gly Val Pro Ala Ile Tyr Tyr Gly Thr Glu Gln Tyr Met Thr
        355                 360                 365

Gly Asp Gly Asp Pro Asn Asn Arg Ala Met Met Thr Ser Phe Asn Thr
    370                 375                 380

Gly Thr Thr Ala Tyr Lys Val Ile Gln Ala Leu Ala Pro Leu Arg Lys
385                 390                 395                 400

Ser Asn Pro Ala Ile Ala Tyr Gly Thr Thr Thr Glu Arg Trp Val Asn
                405                 410                 415
```

Asn Asp Val Leu Ile Ile Glu Arg Lys Phe Gly Ser Ala Ala Leu
            420                 425                 430

Val Ala Ile Asn Arg Asn Ser Ala Ala Tyr Pro Ile Ser Gly Leu
        435                 440                 445

Leu Ser Ser Leu Pro Ala Gly Thr Tyr Ser Asp Val Leu Asn Gly Leu
    450                 455                 460

Leu Asn Gly Asn Ser Ile Thr Val Gly Ser Gly Ala Val Thr Asn
465                 470                 475                 480

Phe Thr Leu Ala Ala Gly Gly Thr Ala Val Trp Gln Tyr Thr Ala Pro
            485                 490                 495

Glu Thr Ser Pro Ala Ile Gly Asn Val Gly Pro Thr Met Gly Gln Pro
            500                 505                 510

Gly Asn Ile Val Thr Ile Asp Gly Arg Gly Phe Gly Gly Thr Ala Gly
            515                 520                 525

Thr Val Tyr Phe Gly Thr Thr Ala Val Thr Gly Ser Gly Ile Val Ser
            530                 535                 540

Trp Glu Asp Thr Gln Ile Lys Ala Val Ile Pro Lys Val Ala Ala Gly
545                 550                 555                 560

Lys Thr Gly Val Ser Val Lys Thr Ser Ser Gly Thr Ala Ser Asn Thr
                565                 570                 575

Phe Lys Ser Phe Asn Val Leu Thr Gly Asp Gln Val Thr Val Arg Phe
            580                 585                 590

Leu Val Asn Gln Ala Asn Thr Asn Tyr Gly Thr Asn Val Tyr Leu Val
            595                 600                 605

Gly Asn Ala Ala Glu Leu Gly Ser Trp Asp Pro Asn Lys Ala Ile Gly
610                 615                 620

Pro Met Tyr Asn Gln Val Ile Ala Lys Tyr Pro Ser Trp Tyr Tyr Asp
625                 630                 635                 640

Val Ser Val Pro Ala Gly Thr Lys Leu Asp Phe Lys Phe Ile Lys Lys
                645                 650                 655

Gly Gly Gly Thr Val Thr Trp Glu Gly Gly Asn His Thr Tyr Thr
                660                 665                 670

Thr Pro Ala Ser Gly Val Gly Thr Val Thr Val Asp Trp Gln Asn
            675                 680                 685

<210> SEQ ID NO 7
<211> LENGTH: 687
<212> TYPE: PRT
<213> ORGANISM: Artificial sequence
<220> FEATURE:
<223> OTHER INFORMATION: Translated from synthetic DNA

<400> SEQUENCE: 7

Ser Pro Asp Thr Ser Val Asp Asn Lys Val Asn Phe Ser Thr Asp Val
1               5                   10                  15

Ile Tyr Gln Ile Val Thr Asp Arg Phe Ala Asp Gly Asp Arg Thr Asn
            20                  25                  30

Asn Pro Ala Gly Asp Ala Phe Ser Gly Asp Arg Ser Asn Leu Lys Leu
        35                  40                  45

Tyr Phe Gly Gly Asp Trp Gln Gly Ile Ile Asp Lys Ile Asn Asp Gly
    50                  55                  60

Tyr Leu Thr Gly Met Gly Val Thr Ala Leu Trp Ile Ser Gln Pro Val
65                  70                  75                  80

Glu Asn Ile Thr Ser Val Ile Lys Tyr Ser Gly Val Asn Asn Thr Ser
                85                  90                  95

```
Tyr His Gly Tyr Trp Ala Arg Asp Phe Lys Gln Thr Asn Asp Ala Phe
             100                 105                 110

Gly Asp Phe Ala Asp Phe Gln Asn Leu Ile Asp Thr Ala His Ala His
        115                 120                 125

Asn Ile Lys Val Val Ile Asp Phe Ala Pro Asn His Thr Ser Pro Ala
    130                 135                 140

Asp Arg Asp Asn Pro Gly Phe Ala Glu Asn Gly Val Leu Tyr Asp Asn
145                 150                 155                 160

Gly Ser Leu Leu Gly Lys Tyr Ser Asn Asp Thr Ala Gly Pro Phe His
                165                 170                 175

His Asn Gly Gly Thr Asp Phe Ser Thr Ile Glu Asp Gly Ile Tyr Lys
            180                 185                 190

Asn Leu Tyr Asp Leu Ala Asp Ile Asn His Asn Asn Asn Ala Met Asp
        195                 200                 205

Ala Tyr Phe Lys Ser Ala Ile Asp Leu Trp Leu Gly Met Gly Val Asp
    210                 215                 220

Gly Ile Arg Phe Asp Ala Val Lys His Met Pro Phe Gly Trp Gln Lys
225                 230                 235                 240

Ser Phe Val Ser Ser Ile Tyr Gly Gly Asp His Pro Val Phe Thr Phe
                245                 250                 255

Gly Glu Trp Tyr Leu Gly Ala Asp Gln Thr Asp Gly Asp Asn Ile Lys
            260                 265                 270

Phe Ala Asn Glu Ser Gly Met Asn Leu Leu Asp Phe Glu Tyr Ala Gln
        275                 280                 285

Glu Val Arg Glu Val Phe Arg Asp Lys Thr Gly Thr Met Lys Asp Leu
    290                 295                 300

Tyr Glu Val Leu Ala Ser Thr Glu Ser Gln Tyr Asp Tyr Ile Asn Asn
305                 310                 315                 320

Met Val Thr Phe Ile Asp Asn His Asp Met Asp Arg Phe Gln Val Ala
                325                 330                 335

Gly Ser Gly Thr Arg Ala Thr Glu Gln Ala Leu Ala Leu Thr Leu Thr
            340                 345                 350

Ser Arg Gly Val Pro Ala Ile Tyr Tyr Gly Thr Glu Gln Tyr Met Thr
        355                 360                 365

Gly Asp Gly Asp Pro Asn Asn Arg Ala Met Met Thr Ser Phe Asn Thr
    370                 375                 380

Gly Thr Thr Ala Tyr Lys Val Ile Gln Ala Leu Ala Pro Leu Arg Lys
385                 390                 395                 400

Ser Asn Pro Ala Ile Ala Tyr Gly Thr Thr Thr Glu Arg Trp Val Asn
                405                 410                 415

Asn Asp Val Leu Ile Ile Glu Arg Lys Phe Gly Ser Ser Ala Ala Leu
            420                 425                 430

Val Ala Ile Asn Arg Asn Ser Ser Ala Ala Tyr Pro Ile Ser Gly Leu
        435                 440                 445

Leu Ser Ser Leu Pro Ala Gly Thr Tyr Ser Asp Val Leu Asn Gly Leu
    450                 455                 460

Leu Asn Gly Asn Ser Ile Thr Val Gly Ser Gly Gly Ala Val Thr Asn
465                 470                 475                 480

Phe Thr Leu Ala Ala Gly Gly Thr Ala Val Trp Gln Tyr Thr Ala Pro
                485                 490                 495

Glu Thr Ser Pro Ala Ile Gly Asn Val Gly Pro Thr Met Gly Gln Pro
            500                 505                 510
```

-continued

Gly Asn Ile Val Thr Ile Asp Gly Arg Gly Phe Gly Thr Ala Gly
            515                 520                 525

Thr Val Tyr Phe Gly Thr Thr Ala Val Thr Gly Ser Gly Ile Val Ser
530                 535                 540

Trp Glu Asp Thr Gln Ile Lys Ala Val Ile Pro Lys Val Ala Ala Gly
545                 550                 555                 560

Lys Thr Gly Val Ser Val Lys Thr Ser Ser Gly Thr Ala Ser Asn Thr
                565                 570                 575

Phe Lys Ser Phe Asn Val Leu Thr Gly Asp Gln Val Thr Val Arg Phe
            580                 585                 590

Leu Val Asn Gln Ala Asn Thr Asn Tyr Gly Thr Asn Val Tyr Leu Val
        595                 600                 605

Gly Asn Ala Ala Glu Leu Gly Ser Trp Asp Pro Asn Lys Ala Ile Gly
    610                 615                 620

Pro Met Tyr Asn Gln Val Ile Ala Lys Tyr Pro Ser Trp Tyr Tyr Asp
625                 630                 635                 640

Val Ser Val Pro Ala Gly Thr Lys Leu Asp Phe Lys Phe Ile Lys Lys
                645                 650                 655

Gly Gly Gly Thr Val Thr Trp Glu Gly Gly Asn His Thr Tyr Thr
            660                 665                 670

Thr Pro Ala Ser Gly Val Gly Thr Val Thr Val Asp Trp Gln Asn
        675                 680                 685

<210> SEQ ID NO 8
<211> LENGTH: 21
<212> TYPE: DNA
<213> ORGANISM: Artificial sequence
<220> FEATURE:
<223> OTHER INFORMATION: Synthetic DNA

<400> SEQUENCE: 8
gcagaaaatg gtgttctgta t                                             21

<210> SEQ ID NO 9
<211> LENGTH: 21
<212> TYPE: DNA
<213> ORGANISM: Artificial sequence
<220> FEATURE:
<223> OTHER INFORMATION: Synthetic DNA

<400> SEQUENCE: 9
gttatcatac agaacaccat t                                             21

<210> SEQ ID NO 10
<211> LENGTH: 21
<212> TYPE: DNA
<213> ORGANISM: Artificial sequence
<220> FEATURE:
<223> OTHER INFORMATION: Synthetic DNA

<400> SEQUENCE: 10
gacaccgctg gcccgttcca t                                             21

<210> SEQ ID NO 11
<211> LENGTH: 21
<212> TYPE: DNA
<213> ORGANISM: Artificial sequence
<220> FEATURE:
<223> OTHER INFORMATION: Synthetic DNA

<400> SEQUENCE: 11
gttgtgatgg aacgggccag c                                             21

<210> SEQ ID NO 12
<211> LENGTH: 24
<212> TYPE: DNA
<213> ORGANISM: Artificial sequence
<220> FEATURE:
<223> OTHER INFORMATION: Synthetic DNA

<400> SEQUENCE: 12
tcactgctgg gttactactc gaat                                          24

<210> SEQ ID NO 13
<211> LENGTH: 24
<212> TYPE: DNA
<213> ORGANISM: Artificial sequence
<220> FEATURE:
<223> OTHER INFORMATION: Synthetic DNA

<400> SEQUENCE: 13
gtcattcgag tagtaaccca gcag                                          24

<210> SEQ ID NO 14
<211> LENGTH: 24
<212> TYPE: DNA
<213> ORGANISM: Artificial sequence
<220> FEATURE:
<223> OTHER INFORMATION: Synthetic DNA

<400> SEQUENCE: 14
tcactgctgg gtgtttactc gaat                                          24

<210> SEQ ID NO 15
<211> LENGTH: 24
<212> TYPE: DNA
<213> ORGANISM: Artificial sequence
<220> FEATURE:
<223> OTHER INFORMATION: Synthetic DNA

<400> SEQUENCE: 15
gtcattcgag taaacaccca gcag                                          24

<210> SEQ ID NO 16
<211> LENGTH: 24
<212> TYPE: DNA
<213> ORGANISM: Artificial sequence
<220> FEATURE:
<223> OTHER INFORMATION: Synthetic DNA

<400> SEQUENCE: 16
tcactgctgg gtggttactc gaat                                          24

<210> SEQ ID NO 17
<211> LENGTH: 24
<212> TYPE: DNA
<213> ORGANISM: Artificial sequence
<220> FEATURE:
<223> OTHER INFORMATION: Synthetic DNA

<400> SEQUENCE: 17
gtcattcgag taaccaccca gcag                                          24

<210> SEQ ID NO 18
<211> LENGTH: 24
<212> TYPE: DNA
<213> ORGANISM: Artificial sequence
<220> FEATURE:
<223> OTHER INFORMATION: Synthetic DNA

<400> SEQUENCE: 18
tcactgctgg gtaaatactc gaat                                    24

<210> SEQ ID NO 19
<211> LENGTH: 24
<212> TYPE: DNA
<213> ORGANISM: Artificial sequence
<220> FEATURE:
<223> OTHER INFORMATION: Synthetic DNA

<400> SEQUENCE: 19
gtcattcgag tatttaccca gcag                                    24

<210> SEQ ID NO 20
<211> LENGTH: 21
<212> TYPE: DNA
<213> ORGANISM: Artificial sequence
<220> FEATURE:
<223> OTHER INFORMATION: Synthetic DNA

<400> SEQUENCE: 20
gcagaaaatg gttctctgta t                                       21

<210> SEQ ID NO 21
<211> LENGTH: 21
<212> TYPE: DNA
<213> ORGANISM: Artificial sequence
<220> FEATURE:
<223> OTHER INFORMATION: Synthetic DNA

<400> SEQUENCE: 21
gttatcatac agagaaccat t                                       21

<210> SEQ ID NO 22
<211> LENGTH: 21
<212> TYPE: DNA
<213> ORGANISM: Artificial sequence
<220> FEATURE:
<223> OTHER INFORMATION: Synthetic DNA

<400> SEQUENCE: 22
gcagaaaatg gtctgctgta t                                       21

<210> SEQ ID NO 23
<211> LENGTH: 22
<212> TYPE: DNA
<213> ORGANISM: Artificial sequence
<220> FEATURE:
<223> OTHER INFORMATION: Synthetic DNA

<400> SEQUENCE: 23
gttatcatac agcagaccat tg                                      22

<210> SEQ ID NO 24
<211> LENGTH: 21
<212> TYPE: DNA
<213> ORGANISM: Artificial sequence
<220> FEATURE:
<223> OTHER INFORMATION: Synthetic DNA

```
<400> SEQUENCE: 24
gacaccgctg gcatgttcca t                                              21

<210> SEQ ID NO 25
<211> LENGTH: 21
<212> TYPE: DNA
<213> ORGANISM: Artificial sequence
<220> FEATURE:
<223> OTHER INFORMATION: Synthetic DNA

<400> SEQUENCE: 25
gttgtgatgg aacatgccag c                                              21
```

METHOD FOR PRODUCING LONG-CHAIN GLYCOSYLATED GENISTEIN

TECHNICAL FIELD

The disclosure relates to a method for producing long-chain glycosylated genistein and belongs to the technical fields of enzyme engineering and fermentation engineering.

BACKGROUND

Genistein, also known as 5,7,4-trihydroxyisoflavone, genisteol or prunetol, is widely distributed in nature, mainly in cereal plants such as soybeans, mung beans, alfalfa, oats, barley, rye, wheat, and corn. Genistein, as a non-estrogen compound with low estrogen-like effects, has an extremely high application prospect in the fields of medicine and health care.

At present, genistein is mainly used for prevention and treatment of diseases such as cardiovascular diseases, female menopausal syndromes, breast hyperplasia, breast cancer, and prostate cancer, and has the characteristic of not killing normal cells when used as a preventive agent for tumor cells. Therefore, genistein is highly valued by the medical field of various countries. However, genistein has low bioavailability due to its high hydrophobicity. Thus the purpose of clinical treatment of diseases is difficult to achieve, and the application of genistein in the fields of medicine and health care is greatly limited. Therefore, how to improve the solubility of genistein in an aqueous solution becomes the focus of attention at home and abroad.

The solubility of genistein diglucoside and genistein triglucoside in water is 3,700 times and 44,000 times higher than that of genistein respectively (see the reference for details: Li D, Roh S A, Shim J H, Mikami B, Baik M Y, Park C S, Park K H. 2005. Glycosylation of genistin into soluble inclusion complex form of cyclic glucans by enzymatic modification. J Agric Food Chem 53:6516-24). Some reports showed that the physiological and biochemical functions of genistein are not affected by glycosylation of genistein (see the reference for details: Chung M J, Kang A Y, Lee K M, Oh E, Jun H J, Kim S Y, Auh J H, Moon T W, Lee S J, Park K H. 2006. Water-soluble genistin glycoside isoflavones up-regulate antioxidant metallothionein expression and scavenge free radicals. J Agric Food Chem 54:3819-26). In addition, glycosylated genistein can be hydrolyzed into glucose and genistein which can be absorbed by the human body in vivo with high safety (see the reference for details: Chung M J, Kang A Y, Lee K M, Oh E, Jun H J, Kim S Y, Auh J H, Moon T W, Lee Si, Park K H. 2006. Water-soluble genistin glycoside isoflavones up-regulate antioxidant metallothionein expression and scavenge free radicals. J Agric Food Chem 54:3819-26). Therefore, the water solubility of genistein can be improved by glycosylation.

Cyclodextrin glycosyltransferase (CGTase or CGT enzyme for short, EC 2.4.1.19) is a common enzyme which can catalyze glycosylation reactions and be used in glycosylation of genistein. On this basis, some researches showed that the longer a sugar chain connected to glycolylated genistein, the higher the water solubility (see the reference for details: Li D, Roh S A, Shim J H, Mikami B, Baik M Y, Park C S, Park K H. 2005. Glycosylation of genistin into soluble inclusion complex form of cyclic glucans by enzymatic modification. J Agric Food Chem 53:6516-24). Therefore, the production of a large amount of long-chain glycosylated genistein is very important to improve the application value.

However, currently most cyclodextrin glucosyltransferases have lower synthesis efficiency for long-chain glycosylated genistein than short-chain glycosylated genistein, and thus the synthetic yield of long-chain glycosylated genistein by cyclodextrin glucosyltransferases is greatly limited. Therefore, it is urgent to find a method for producing long-chain glycosylated genistein with high yield.

SUMMARY

The disclosure provides a cyclodextrin glucosyltransferase mutant, wherein the cyclodextrin glucosyltransferase mutant is obtained by mutating alanine at position 156 and leucine at position 174 of cyclodextrin glucosyltransferase with an initial amino acid sequence shown as SEQ ID NO: 1;

or, the cyclodextrin glucosyltransferase mutant is obtained by mutating alanine at position 156, leucine at position 174 and alanine at position 166 of cyclodextrin glucosyltransferase with an initial amino acid sequence shown as SEQ ID NO: 1.

In an embodiment of the disclosure, the cyclodextrin glucosyltransferase mutant is obtained by mutating alanine at position 156 into valine and leucine at position 174 into proline of cyclodextrin glucosyltransferase with an initial amino acid sequence shown as SEQ ID NO: 1 and named A156V/L174P;

or, the cyclodextrin glucosyltransferase mutant is obtained by mutating alanine at position 156 into valine, leucine at position 174 into proline and alanine at position 166 into tyrosine of cyclodextrin glucosyltransferase with an initial amino acid sequence shown as SEQ ID NO: 1 and named A156V/L174P/A166Y;

or, the cyclodextrin glucosyltransferase mutant is obtained by mutating alanine at position 156 into valine, leucine at position 174 into proline and alanine at position 166 into valine of cyclodextrin glucosyltransferase with an initial amino acid sequence shown as SEQ ID NO: 1 and named A156V/L174P/A166V;

or, the cyclodextrin glucosyltransferase mutant is obtained by mutating alanine at position 156 into valine, leucine at position 174 into proline and alanine at position 166 into glycine of cyclodextrin glucosyltransferase with an initial amino acid sequence shown as SEQ ID NO: 1 and named A156V/L174P/A166G;

or, the cyclodextrin glucosyltransferase mutant is obtained by mutating alanine at position 156 into valine, leucine at position 174 into proline and alanine at position 166 into lysine of cyclodextrin glucosyltransferase with an initial amino acid sequence shown as SEQ ID NO: 1 and named A156V/L174P/A166K.

In an embodiment of the disclosure, an amino acid sequence of the cyclodextrin glucosyltransferase mutant is SEQ ID NO: 3, SEQ ID NO: 4, SEQ ID NO: 5, SEQ ID NO: 6 or SEQ ID NO: 7.

In an embodiment of the disclosure, a nucleotide sequence for encoding cyclodextrin glucosyltransferase is shown as SEQ ID NO: 2.

The disclosure also provides a gene for encoding the cyclodextrin glucosyltransferase mutant.

The disclosure also provides a recombinant plasmid carrying the gene.

In an embodiment of the disclosure, a vector of the recombinant plasmid is a plasmid pET-20b(+), a plasmid pET-22b(+) or a plasmid pET-28a(+).

In an embodiment of the disclosure, a vector of the recombinant plasmid is a plasmid pET-20b(+).

The disclosure also provides a host cell carrying the gene or the recombinant plasmid.

In an embodiment of the disclosure, the host cell is a bacterium or a fungus.

In an embodiment of the disclosure, the host cell is *Escherichia coli*.

The disclosure also provides a preparation method of the above cyclodextrin glucosyltransferase mutants, comprising the following steps: inoculating a fermentation culture medium with the host cells for fermentation to obtain a fermentation solution; centrifuging the fermentation solution to obtain a fermentation supernatant; and separating the fermentation supernatant to obtain the cyclodextrin glucosyltransferase mutants.

The disclosure also provides a method for producing long-chain glycosylated genistein, comprising the following steps: making a reaction system containing maltodextrin, genistein and cyclodextrin glucosyltransferase (CGTase or CGT enzyme for short, EC 2.4.1.19) undergo a reaction at a pH of 4-8, a temperature of 30-60° C. and a rotation speed of 120-180 rpm to obtain a reaction solution; and separating the reaction solution to obtain long-chain glycosylated genistein, wherein the cyclodextrin glucosyltransferase is one or more of cyclodextrin glucosyltransferases with amino acid sequences shown as SEQ ID NO: 1, SEQ ID NO: 3, SEQ ID NO: 4, SEQ ID NO: 5, SEQ ID NO: 6 or SEQ ID NO: 7. The long-chain glycosylated genistein refers to genistein tetraglucoside, genistein pentaglucoside and/or genistein hexaglucoside.

In an embodiment of the disclosure, the method comprises the following steps: dissolving genistein in dimethyl sulfoxide to prepare a genistein solution; dissolving maltodextrin in a buffer A to prepare a maltodextrin solution; dissolving cyclodextrin glucosyltransferase in a buffer B to prepare an enzyme solution; mixing the genistein solution, the maltodextrin solution and the enzyme solution to obtain a reaction system; making the reaction system undergo a reaction at a pH of 4-8, a temperature of 30-60° C. and a rotation speed of 120-180 rpm to obtain a reaction solution; and separating the reaction solution to obtain long-chain glycosylated genistein.

In an embodiment of the disclosure, the pH of the reaction is 4 or 8, and the temperature is 45-50° C.

In an embodiment of the disclosure, the cyclodextrin glucosyltransferase is a cyclodextrin glucosyltransferase with the amino acid sequence shown as SEQ ID NO: 4.

In an embodiment of the disclosure, the buffer A is a PBS buffer, a citrate buffer or a sodium acetate buffer.

In an embodiment of the disclosure, the buffer B is a PBS buffer, a citrate buffer or a sodium acetate buffer.

In an embodiment of the disclosure, the concentration of the buffer A is 25-75 mmol/L.

In an embodiment of the disclosure, the concentration of the buffer B is 25-75 mmol/L.

In an embodiment of the disclosure, the concentration of the genistein solution is 5-15 g/L.

In an embodiment of the disclosure, the concentration of the maltodextrin solution is 20-60 g/L.

In an embodiment of the disclosure, the concentration of the enzyme solution is 10-20 U/L.

In an embodiment of the disclosure, the volume ratio of the genistein solution to the maltodextrin solution to the enzyme solution is (2-4):(4-6):(1-3).

In an embodiment of the disclosure, the reaction time is 20-24 hours.

The disclosure also provides application of the cyclodextrin glucosyltransferase mutants or the genes or the recombinant plasmids or the host cells or the preparation method or the method above in production of long-chain glycosylated genistein.

The disclosure provides cyclodextrin glucosyltransferase mutants A156V/L174P, A156V/L174P/A166Y, A156V/L174P/A166V, A156V/L174P/A166G and A156V/L174P/A166K with high specificity toward long-chain glycosylated genistein products. Compared with the yield of long-chain glycosylated genistein produced by using wild-type cyclodextrin glucosyltransferase and by using maltodextrin as a glycosyl donor and genistein as a glycosyl receptor, the yield of long-chain glycosylated genistein produced by using the cyclodextrin glucosyltransferase mutants A156V/L174P, A156V/L174P/A166Y, A156V/L174P/A166V, A156V/L174P/A166G and A156V/L174P/A166K of the disclosure and by using maltodextrin as a glycosyl donor and genistein as a glycosyl receptor is increased by 62.5%, 165%, 112.5%, 112.5% and 59.4% respectively.

The disclosure provides a method for producing long-chain glycosylated genistein with high yield. Using this method to produce long-chain glycosylated genistein can increase the content of long-chain glycosylated genistein in a reaction solution and the ratio of the content of long-chain glycosylated genistein in the reaction solution to the content of total glycosylated genistein in the reaction solution. The content of long-chain glycosylated genistein in the reaction solution can be increased to 10.3 g/L, and the ratio of the content of long-chain glycosylated genistein in the reaction solution to the content of total glycosylated genistein in the reaction solution can be increased to 70%.

DETAILED DESCRIPTION

Figure 1:
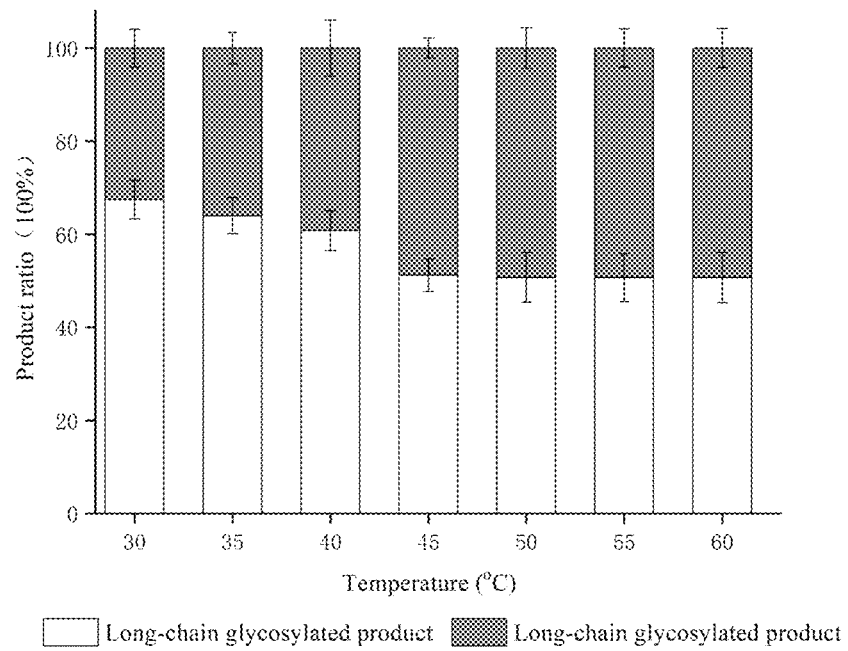
FIG. 1 shows the effect of reaction temperature on the ratio of the molar content of short-chain glycosylated genistein and long-chain glycosylated genistein in a reaction solution to the molar content of total glycosylated genistein in the reaction solution.

The disclosure is further explained below in conjunction with specific examples.

*E. coli* JM109 and *E. Coli* BL21(DE3) involved in the following examples were purchased from TakaRa (Dalian, China), and the plasmid pET-20b(+) is purchased from Novagen (the above bacterial strain *E. coli* BL21(DE3) can be purchased and do not need to be preserved according to patent procedures).

Culture Media Involved in the Following Examples are as Follows:

An LB liquid culture medium: yeast powder 5.0 g·L$^{-1}$, tryptone 10.0 g·L$^{-1}$, NaCl 10.0 g·L$^{-1}$, and ampicillin 100 μg·L$^{-1}$.

An LB solid culture medium: yeast powder 5.0 g·L$^{-1}$, tryptone 10.0 g·L$^{-1}$, NaCl 10.0 g·L$^{-1}$, agar powder 15 g·L$^{-1}$, and ampicillin 100 μg·L$^{-1}$.

Detection Methods Involved in the Following Examples are as Follows:

A cyclodextrin glucosyltransferase activity determination method: 0.1 mL of an enzyme solution was taken and added into 0.9 mL of a soluble starch solution with a concentration of 30 g·L$^{-1}$ pre-prepared with a 50 mM phosphate buffer (pH 6.5) for a reaction at 40° C. for 10 minutes, 1.0 mL of 1.0 M hydrochloric acid was added to stop the reaction, then 1.0 mL of 0.1 mM methyl orange prepared with a 50 mM phosphate buffer was added, the mixture was subjected to heat preservation at 16° C. for 20 minutes, and the absorbance was measured at 505 nm.

Definition of cyclodextrin glucosyltransferase activity: Under these conditions, the enzyme amount required to generate 1 μmol α-cyclodextrin per minute was one unit of enzyme activity.

Example 1: Preparation and Expression of Different Cyclodextrin Glucosyltransferases Specific steps were as follows:

A gene encoding cyclodextrin glucosyltransferase with the amino acid sequence shown as SEQ ID NO: 1 (the nucleotide sequence of the gene was shown as SEQ ID NO: 2) was chemically synthesized; the obtained gene was ligated with the plasmid pET-20b(+) after being digested with double enzymes (Nco I and Xho I), and then transferred into *E. coli* JM109, the transformed product was spread on an LB solid culture medium and cultured at 37° C. for 8 hours, transformants were picked from the LB solid culture medium, an LB liquid culture medium was inoculated with the transformants for culture at 37° C. for 10 hours, and then a plasmid was extracted and sequenced to obtain a correctly sequenced recombinant plasmid pET20b-CGT; the correctly sequenced recombinant plasmid pET20b-CGT was transformed into *E. coli* BL21 (DE3) to obtain recombinant *E. coli* pET20b-CGT/*E. coli* BL21.

By using a whole plasmid PCR technology, the obtained recombinant plasmid pET20b-CGT was used as a template for site-directed mutation to obtain mutants A156V/L174P (the amino acid sequence shown as SEQ ID NO: 3), A156V/L174P/A166Y (the amino acid sequence shown as SEQ ID NO: 4), A156V/L174P/A166V (the amino acid sequence shown as SEQ ID NO: 5), A156V/L174P/A166G (the amino acid sequence shown as SEQ ID NO: 6), A156V/L174P/A166K (the amino acid sequence shown as SEQ ID NO: 7), A156S, A156L and L174M.

Primers used for mutation of A156V were as follows:

```
Forward primer:
                                         (SEQ ID NO: 8)
5'-GCAGAAAATGGTGTTCTGTAT-3'.

Reverse primer:
                                         (SEQ ID NO: 9)
5'-GTTATCATACAGAACACCATT-3'.
```

Primers used for mutation of L174P were as follows:

```
Forward primer:
                                        (SEQ ID NO: 10)
5'-GACACCGCTGGCCCGTTCCAT-3'.
```

```
Reverse primer:
                                        (SEQ ID NO: 11)
5'-GTTGTGATGGAACGGGCCAGC-3'.
```

Primers used for mutation of A166Y were as follows:

```
Forward primer:
                                        (SEQ ID NO: 12)
5'-TCACTGCTGGGTTACTACTCGAAT-3'.

Reverse primer:
                                        (SEQ ID NO: 13)
5'-GTCATTCGAGTAGTAACCCAGCAG-3'.
```

Primers used for mutation of A166V were as follows:

```
Forward primer:
                                        (SEQ ID NO: 14)
5'-TCACTGCTGGGTGTTTACTCGAAT-3'.

Reverse primer:
                                        (SEQ ID NO: 15)
5'-GTCATTCGAGTAAACACCCAGCAG-3'.
```

Primers used for mutation of A166G were as follows:

```
Forward primer:
                                        (SEQ ID NO: 16)
5'-TCACTGCTGGGTGGTTACTCGAAT-3'.

Reverse primer:
                                        (SEQ ID NO: 17)
5'-GTCATTCGAGTAACCACCCAGCAG-3'.
```

Primers used for mutation of A166K were as follows:

```
Forward primer:
                                        (SEQ ID NO: 18)
5'-TCACTGCTGGGTAAATACTCGAAT-3'.

Reverse primer:
                                        (SEQ ID NO: 19)
5'-GTCATTCGAGTATTTACCCAGCAG-3'.
```

Primers used for mutation of A156S were as follows:

```
Forward primer:
                                        (SEQ ID NO: 20)
5'-GCAGAAAATGGTTCTCTGTAT-3'.

Reverse primer:
                                        (SEQ ID NO: 21)
5'-GTTATCATACAGAGAACCATT-3'.
```

Primers used for mutation of A156L were as follows:

```
Forward primer:
                                        (SEQ ID NO: 22)
5'-GCAGAAAATGGTCTGCTGTAT-3'.

Reverse primer:
                                        (SEQ ID NO: 23)
5'-GTTATCATACAGCAGACCATTG-3'.
```

Primers used for mutation of L174M were as follows:

```
Forward primer:
                                        (SEQ ID NO: 24)
5'-GACACCGCTGGCATGTTCCAT-3'.
```

-continued

Reverse primer:
(SEQ ID NO: 25)
5'-GTTGTGATGGAACATGCCAGC-3'.

PCR reaction systems included: 5*PrimeSTAR Buffer (Mg' Plus) 5 μL, 2.5 mM dNTPs 4 μL, 10 μM forward primer 1 μL, 10 μM reverse primer 1 μL, template DNA 1 μL, 2.5 U/μL PrimeSTAR Taq HS 0.5 μL, double distilled water added to 50 μL.

PCR product amplification conditions included: pre-denaturation at 98° C. for 3 minutes; then amplification at 98° C. for 10 seconds, 57° C. for 15 seconds and 72° C. for 6 minutes in 30 cycles; finally heat preservation at 72° C. for 10 minutes.

PCR amplification products were detected by 1% agarose gel electrophoresis. After the detection, 0.5 μL of methylated template digestion enzyme (Dpn I) was added into 10 μL of the amplification products, pipette tip blowing and suction was carried out for uniform mixing, a reaction was carried out at 37° C. for 1.5 hours, the amplification products after Dpn I treatment were transformed into E. coli JM109, transformed products were spread on an LB solid culture medium and cultured at 37° C. for 8 hours, transformants were picked from the LB solid culture medium, an LB liquid culture medium was inoculated with the transformants for culture at 37° C. for 10 hours, and then a plasmid was extracted and sequenced to obtain a correctly sequenced recombinant plasmid containing genes for encoding the mutants A156V/L174P, A156V/L174P/A166Y, A156V/L174P/A166V, A156V/L174P/A166G, A156V/L174P/A166K, A156S, A156L and L174M; the correctly sequenced recombinant plasmid was transferred into E. coli BL21 (DE3) to obtain recombinant E. coli containing genes for encoding the mutants A156V/L174P, A156V/L174P/A166Y, A156V/L174P/A166V, A156V/L174P/A166G, A156V/L174P/A166K, A156S, A156L and L174M.

The obtained recombinant E. coli pET20b-CGT/E. coli BL21 and the recombinant E. coli containing genes for encoding the mutants A156V/L174P, A156V/L174P/A166Y, A156V/L174P/A166V, A156V/L174P/A166G, A156V/L174P/A166K, A156S, A156L and L174M were spread on an LB solid culture medium and cultured at 37° C. for 8-10 hours to obtain a single colony; the single colony was picked, and an LB liquid culture medium was inoculated with the single colony for culture at 37° C. for 12-14 hours to obtain a seed solution; an LB liquid culture medium was inoculated with the seed solution according to the inoculation amount of 4% (v/v) for culture at 30° C. and 120 rpm until $OD_{600}$ was equal to 0.6, and IPTG with a final concentration of 0.01 mM was added into a fermentation broth and continuously subjected to induction culture at 25° C. and 120 rpm for 90 hours to obtain a fermentation solution; after the fermentation solution was centrifuged at 4° C. and 1,000 rpm for 20 minutes, a fermentation supernatant was collected; 70% solid ammonium sulfate was added into the fermentation supernatant for salting out overnight, centrifugation was carried out at 4° C. and 10,000 rpm for 20 minutes, and a precipitate was taken, dissolved in an appropriate amount of a buffer A containing 20 mM sodium phosphate, 0.5 M sodium chloride, and 20 mM imidazole and having a pH of 7.4, dialyzed in the buffer A overnight, filtered through a 0.22 μm membrane and prepared into a loading sample; after an Ni affinity column was equilibrated with the buffer A, the loading sample was completely sucked into the Ni column and then eluted with the buffer A, a buffer A containing 20-480 mM imidazole and a buffer A containing 480 mM imidazole separately at a flow rate of 1 mL/min, the detection wavelength was 280 nm, and eluates having cyclodextrin glucosyltransferase activity were collected separately; after active components were dialyzed in a 50 mM sodium phosphate buffer (pH=6) overnight, pure enzymes of the mutants A156V/L174P, A156V/L174P/A166Y, A156V/L174P/A166V, A156V/L174P/A166G, A156V/L174P/A166K, A156S, A156L and L174M were obtained and freeze-dried for later use.

Example 2: Specificity of Different Cyclodextrin Glucosyltransferases to Different Glycosylated Genistein Products Specific steps were as follows:

Genistein (purchased from Sigma) was dissolved in dimethyl sulfoxide (DMSO) to prepare a genistein solution with a final concentration of 7.5 g/L; maltodextrin (purchased from Shanghai Sangon Biotech Co., Ltd.) was dissolved in a PBS buffer (50 mM, pH 6.5) to prepare a maltodextrin solution with a final concentration of 40 g/L; the freeze-fried pure enzymes of the mutants A156V/L174P, A156V/L174P/166Y, A156V/L174P/A166V, A156V/L174P/A166G, A156V/L174P/A166K, A156S, A156L and L174M obtained in Example 1 were dissolved in a PBS buffer (50 mM, pH 6.5) separately to prepare a CGTase enzyme solution with a final concentration of 15 U/L; 300 μL of the genistein solution, 500 μL of the maltodextrin solution and 200 μL of the CGTase enzyme solution were taken separately, mixed in a 2 mL vial with a lid and placed in a shaker for slow shaking at 40° C. and 120 rpm for 20-24 hours to obtain a reaction solution.

The molar content of short-chain glycosylated genistein (here the short-chain glycosylated genistein was a mixture of monoglycosylated genistein, diglycosylated genistein and triglycosylated genistein) and long-chain glycosylated genistein (here the long-chain glycosylated genistein was a mixture of tetraglycosylated genistein, pentaglycosylated genistein and hexaglycosylated genistein) in the reaction solution was detected by HPLC, the ratio (%) of the molar content of short-chain glycosylated genistein and long-chain glycosylated genistein in the reaction solution to the molar content of total glycosylated genistein in the reaction solution and the content (g/L) of short-chain glycosylated genistein and long-chain glycosylated genistein in the reaction solution were calculated, and detection results were shown in Tables 1 to 2. A method for detecting the ratio (%) of the content of short-chain glycosylated genistein and long-chain glycosylated genistein in the reaction solution to the content of total glycosylated genistein in the reaction solution by HPLC included that the reaction solution was filtered through a 0.22 μm filter membrane, and an Amethyst C18-H column (4.6*250 mm, Sepax, America) was used for detection (see Table 3 for specific detection conditions). The content of long-chain glycosylated genistein=the molar content of hexaglycosylated genistein*the molecular weight of hexaglycosylated genistein+ the molar content of pentaglycosylated genistein*the molecular weight of pentaglycosylated genistein+ the molar content of tetraglycosylated genistein*the molecular weight of tetraglycosylated genistein, and the content of short-chain glycosylated genistein=the molar content of triglycosylated genistein*the molecular weight of triglycosylated genistein+ the molar content of diglycosylated genistein*the molecular weight of diglycosylated genistein+ the molar content of monoglycosylated genistein*the molecular weight of monoglycosylated genistein.

It can be seen from Tables 1 to 2 that only the specificity of the mutants A156V/L174P, A156V/L174P/A166Y, A156V/L174P/A166V, A156V/L174P/A166G and A156V/L174P/A166K to long-chain glycosylated genistein products was high and was significantly improved in comparison with that of a wild type.

Compared with the yield of long-chain glycosylated genistein produced by using wild-type cyclodextrin glucosyltransferase and by using maltodextrin as a glycosyl donor and genistein as a glycosyl receptor, the yield of long-chain glycosylated genistein produced by using the mutant A156V/L174P and by using maltodextrin as a glycosyl donor and genistein as a glycosyl receptor was increased by 62.5%.

Compared with the yield of long-chain glycosylated genistein produced by using wild-type cyclodextrin glucosyltransferase and by using maltodextrin as a glycosyl donor and genistein as a glycosyl receptor, the yield of long-chain glycosylated genistein produced by using the mutant A156V/L174P/A166Y and by using maltodextrin as a glycosyl donor and genistein as a glycosyl receptor was increased by 165%.

Compared with the yield of long-chain glycosylated genistein produced by using wild-type cyclodextrin glucosyltransferase and by using maltodextrin as a glycosyl donor and genistein as a glycosyl receptor, the yield of long-chain glycosylated genistein produced by using the mutant A156V/L174P/A166V and by using maltodextrin as a glycosyl donor and genistein as a glycosyl receptor was increased by 112.5%.

Compared with the yield of long-chain glycosylated genistein produced by using wild-type cyclodextrin glucosyltransferase and by using maltodextrin as a glycosyl donor and genistein as a glycosyl receptor, the yield of long-chain glycosylated genistein produced by using the mutant A156V/L174P/A166G and by using maltodextrin as a glycosyl donor and genistein as a glycosyl receptor was increased by 37.5%.

Compared with the yield of long-chain glycosylated genistein produced by using wild-type cyclodextrin glucosyltransferase and by using maltodextrin as a glycosyl donor and genistein as a glycosyl receptor, the yield of long-chain glycosylated genistein produced by using the mutant A156V/L174P/A166K and by using maltodextrin as a glycosyl donor and genistein as a glycosyl receptor was increased by 59.4%.

Table 1 The ratio (%) of the molar content of short-chain glycosylated genistein and long-chain glycosylated genistein in a reaction solution obtained by a reaction of different cyclodextrin glucosyltransferases to the molar content of total glycosylated genistein in the reaction solution

| Group | Long-chain glycosylated genistein | Short-chain glycosylated genistein |
| --- | --- | --- |
| Wild type | 15 | 85 |
| A156S | 7 | 93 |
| A156L | 5 | 95 |
| L174M | 6 | 94 |
| A156V/L174P | 25 | 75 |
| A156V/L174P/A166V | 29 | 71 |
| A156V/L174P/A166G | 20 | 80 |
| A156V/L174P/A166K | 24 | 76 |
| A156V/L174P/A166Y | 40 | 60 |

Table 2 The content (g/L) of short-chain glycosylated genistein and long-chain glycosylated genistein in a reaction solution obtained by a reaction of different cyclodextrin glucosyltransferases

| Group | Long-chain glycosylated genistein | Short-chain glycosylated genistein |
| --- | --- | --- |
| Wild type | 3.2 | 11.4 |
| A156S | 1.2 | 8.83 |
| A156L | 0.7 | 7.64 |
| L174M | 1.0 | 8.87 |
| A156V/L174P | 5.2 | 9.7 |
| A156V/L174P/A166V | 6.8 | 9.5 |
| A156V/L174P/A166G | 4.4 | 10.9 |
| A156V/L174P/A166K | 5.1 | 10.1 |
| A156V/L174P/A166Y | 8.5 | 8.0 |

Table 3 Conditions for detecting the content of short-chain glycosylated genistein and long-chain glycosylated genistein in a reaction solution by HPLC

| Instrument | Model and content |
| --- | --- |
| Liquid chromatograph | An Agilent 1260 Infinity HPLC system |
| Chromatographic column | 250*4.6 mm Diamonsil C18 column |
| Mobile phase | A (water/phosphoric acid, 100:0.1, v/v) B (acetonitrile) |
| Elution conditions | 0-2 min 15% B; 2-17 min 15-85% B; 17-25 min 85% B; and 25-27 min 85-15% B |
| Flow rate | 0.8 mL/min |
| Injection volume | 10 μL |
| Column temperature | 30° C. |

Example 3: The Effect of Reaction Temperature on the Yield of Long-Chain Glycosylated Genistein Specific steps were as follows:

On the basis of Example 2, the mutant A156V/L174P/A166Y with the highest specificity to long-chain glycosylated genistein products was selected, and the reaction temperature was changed into 30° C., 35° C., 40° C., 45° C., 50° C., 55° C. and 60° C. separately.

With reference to Example 2, the molar content of short-chain glycosylated genistein (here the short-chain glycosylated genistein was a mixture of monoglycosylated genistein, diglycosylated genistein and triglycosylated genistein) and long-chain glycosylated genistein (here the long-chain glycosylated genistein was a mixture of tetraglycosylated genistein, pentaglycosylated genistein and hexaglycosylated genistein) in a reaction solution was detected by HPLC, the ratio (%) of the molar content of short-chain glycosylated genistein and long-chain glycosylated genistein in the reaction solution to the molar content of total glycosylated genistein in the reaction solution and the content (g/L) of short-chain glycosylated genistein and long-chain glycosylated genistein in the reaction solution were calculated, and detection results were shown in Table 4 and FIG. 1.

It can be seen from Table 4 that when the temperature was 45-50° C., the yield of long-chain glycosylated genistein produced by using the mutant A156V/L174P/A166Y and by using maltodextrin as a glycosyl donor and genistein as a glycosyl receptor was the highest, could reach 10.2-10.4 g/L, and was increased by 21.4-23.8% in comparison with that when the temperature was 40° C.

It can be seen from FIG. 1 that the higher the temperature, the higher the ratio of the molar content of long-chain glycosylated genistein in a reaction solution obtained by a reaction of the mutant A156V/L174P/A166Y to the molar content of total glycosylated genistein in the reaction solution, and the ratio could reach 49% and was increased by 21% in comparison with that when the temperature was 40° C.

It can be seen that when long-chain glycosylated genistein was produced by using the mutant A156V/L174P/A166Y and by using maltodextrin as a glycosyl donor and genistein as a glycosyl receptor, the temperature should be controlled to be 45-50° C.

Table 4 The content (g/L) of short-chain glycosylated genistein and long-chain glycosylated genistein in a reaction solution obtained by a reaction at different temperatures

| Temperature | Long-chain glycosylated genistein | Short-chain glycosylated genistein |
| --- | --- | --- |
| 30° C. | 6.8 | 8.9 |
| 35° C. | 7.6 | 8.5 |
| 40° C. | 8.4 | 8.0 |
| 45° C. | 10.1 | 6.8 |
| 50° C. | 10.0 | 6.6 |
| 55° C. | 8.9 | 5.6 |
| 60° C. | 5.7 | 3.6 |

Example 4: The Effect of Reaction pH on the Yield of Long-Chain Glycosylated Genistein Specific steps were as follows:

On the basis of Example 2, the mutant A156V/L174P/A166Y with the highest specificity to long-chain glycosylated genistein products was selected, the reaction temperature was controlled to be 50° C., and the reaction pH was changed into 4, 5, 6, 7 and 8 separately.

Figure 2:
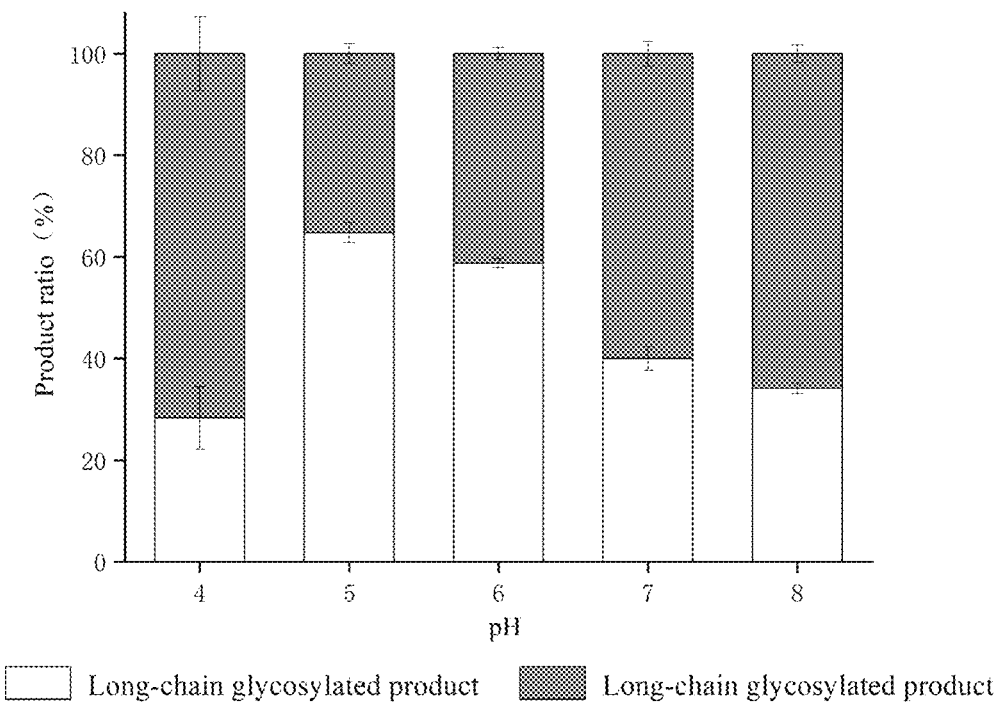
FIG. 2 shows the effect of reaction pH on the ratio of the molar content of short-chain glycosylated genistein and long-chain glycosylated genistein in a reaction solution to the molar content of total glycosylated genistein in the reaction solution.

With reference to Example 2, the molar content of short-chain glycosylated genistein (here the short-chain glycosylated genistein was a mixture of monoglycosylated genistein, diglycosylated genistein and triglycosylated genistein) and long-chain glycosylated genistein (here the long-chain glycosylated genistein was a mixture of tetraglycosylated genistein, pentaglycosylated genistein and hexaglycosylated genistein) in a reaction solution was detected by HPLC, the ratio (%) of the molar content of short-chain glycosylated genistein and long-chain glycosylated genistein in the reaction solution to the molar content of total glycosylated genistein in the reaction solution and the content (g/L) of short-chain glycosylated genistein and long-chain glycosylated genistein in the reaction solution were calculated, and detection results were shown in Table 5 and FIG. 2.

It can be seen from Table 5 that when the pH was 4 or 8, the yield of long-chain glycosylated genistein produced by using the mutant A156V/L174P/A166Y and by using maltodextrin as a glycosyl donor and genistein as a glycosyl receptor was the highest, could reach 10.2-10.3 g/L, and was increased by 20% in comparison with that when the pH was 6.5.

It can be seen from FIG. 2 that when the pH was 4, the ratio of the molar content of long-chain glycosylated genistein in a reaction solution obtained by a reaction of the mutant A156V/L174P/A166Y to the molar content of total glycosylated genistein in the reaction solution was the highest, could reach 70% and was increased by 30% in comparison with that when the pH was 6.5.

It can be seen that when long-chain glycosylated genistein was produced by using the mutant A156V/L174P/A166Y and by using maltodextrin as a glycosyl donor and genistein as a glycosyl receptor, the pH should be controlled to be 4.

Table 5 The content (g/L) of short-chain glycosylated genistein and long-chain glycosylated genistein in a reaction solution obtained by a reaction with different pH values

| pH | Long-chain glycosylated genistein | Short-chain glycosylated genistein |
| --- | --- | --- |
| 4 | 10.2 | 2.6 |
| 5 | 7.2 | 8.8 |
| 6 | 8.5 | 8.0 |
| 7 | 9.7 | 5.5 |
| 8 | 10.3 | 3.6 |

What is claimed is:

1. A cyclodextrin glucosyltransferase mutant, comprising the amino acid sequence of SEQ ID NO: 3, SEQ ID NO: 4, SEQ ID NO: 5, SEQ ID NO: 6 or SEQ ID NO: 7.

2. A gene for encoding the cyclodextrin glucosyltransferase mutant of claim 1.

3. A recombinant plasmid carrying the gene of claim 2.

4. The recombinant plasmid of claim 3, wherein a vector of the recombinant plasmid is a plasmid pET-20b(+), a plasmid pET-22b(+) or a plasmid pET-28a(+).

5. A host cell carrying the gene of claim 2.

6. The host cell of claim 5, wherein the host cell is a bacterium or a fungus.

7. A preparation method of the cyclodextrin glucosyltransferase mutant of claim 1, comprising the following steps: inoculating a fermentation culture medium with a host cell capable of expressing the cyclodextrin glucosyltransferase mutant for fermentation to obtain a fermentation solution; centrifuging the fermentation solution to obtain a fermentation supernatant; and separating the fermentation supernatant to obtain the cyclodextrin glucosyltransferase mutant.

8. A method of use of a cyclodextrin glucosyltransferase mutant for producing long-chain glycosylated genistein, comprising the following steps:
making a reaction system containing maltodextrin, genistein and the cyclodextrin glucosyltransferase mutant, performing a reaction at a pH of 4-8, a temperature of 30-60° C. and a rotation speed of 120-180 rpm to obtain a reaction solution; and
separating the reaction solution to obtain the long-chain glycosylated genistein, wherein the cyclodextrin glucosyltransferase is one or more cyclodextrin glucosyltransferases mutant with the amino acid sequences set forth as SEQ ID NO: 3, SEQ ID NO: 4, SEQ ID NO: 5, SEQ ID NO: 6 and SEQ ID NO: 7.

9. The method of claim 8, wherein the method further comprises the following steps: dissolving genistein in dimethyl sulfoxide to prepare a genistein solution; dissolving maltodextrin in a buffer A to prepare a maltodextrin solution; dissolving cyclodextrin glucosyltransferase in a buffer B to prepare an enzyme solution; and mixing the genistein solution, the maltodextrin solution and the enzyme solution to obtain the reaction system; making the reaction system undergo a reaction at a pH of 4-8, a temperature of 30-60° C. and a rotation speed of 120-180 rpm to obtain a reaction solution; and separating the reaction solution to obtain the long-chain glycosylated genistein.

10. The method of claim 9, wherein the pH of the reaction is 4 or 8, and the temperature is 45-50° C.

11. The method of claim 8, wherein the cyclodextrin glucosyltransferase is a cyclodextrin glucosyltransferase with the amino acid sequence set forth as SEQ ID NO: 4.

12. The method of claim 9, wherein the buffer A is a PBS buffer, a citrate buffer or a sodium acetate buffer.

13. The method of claim 9, wherein the buffer B is a PBS buffer, a citrate buffer or a sodium acetate buffer.

14. The method of claim 9, wherein a concentration of the genistein solution is 5-15 g/L.

15. The method of claim 9, wherein a concentration of the enzyme solution is 10-20 U/L.

16. The method of claim 9, wherein a volume ratio of the genistein solution to the maltodextrin solution to the enzyme solution is (2-4):(4-6):(1-3).

* * * * *